(12) United States Patent
Lee et al.

(10) Patent No.: US 11,978,146 B2
(45) Date of Patent: May 7, 2024

(54) APPARATUS AND METHOD FOR RECONSTRUCTING THREE-DIMENSIONAL IMAGE

(71) Applicant: Seoul National University R&DB Foundation, Seoul (KR)

(72) Inventors: Dong Young Lee, Seoul (KR); Yu Kyeong Kim, Seoul (KR); Jae Sung Lee, Seoul (KR); Min Soo Byun, Seoul (KR); Seong A Shin, Seoul (KR); Seung Kwan Kang, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 516 days.

(21) Appl. No.: 17/276,291

(22) PCT Filed: Sep. 18, 2019

(86) PCT No.: PCT/KR2019/012086
§ 371 (c)(1),
(2) Date: Mar. 15, 2021

(87) PCT Pub. No.: WO2020/060196
PCT Pub. Date: Mar. 26, 2020

(65) Prior Publication Data
US 2022/0028154 A1  Jan. 27, 2022

(30) Foreign Application Priority Data

Sep. 18, 2018  (KR) .................. 10-2018-0111678
Sep. 17, 2019  (KR) .................. 10-2019-0114294

(51) Int. Cl.
*G06T 7/00*  (2017.01)
*G06F 18/21*  (2023.01)
(Continued)

(52) U.S. Cl.
CPC ............ *G06T 15/005* (2013.01); *G06F 18/21* (2023.01); *G06T 3/4007* (2013.01);
(Continued)

(58) Field of Classification Search
CPC ... G06T 15/005; G06T 3/4007; G06T 7/0012; G06T 2207/20081; G06T 2207/20084;
(Continued)

(56) References Cited

U.S. PATENT DOCUMENTS 9,483,813 B2    11/2016  Nakano et al.
2009/0124885 A1*  5/2009  Umeda ................ A61B 5/0037
                                                600/410
(Continued)

FOREIGN PATENT DOCUMENTS

KR      10-1659578        9/2016
KR      10-2018-0021635   3/2018
(Continued)

OTHER PUBLICATIONS

KIPO, PCT Search Report & Written Opinion of PCT/KR2019/012086 dated Jan. 8, 2020.
(Continued)

*Primary Examiner* — Ali Bayat
(74) *Attorney, Agent, or Firm* — LEX IP MEISTER, PLLC

(57) ABSTRACT

The present invention relates to a three-dimensional reconstructing method of a 2D medical image. A three-dimensional reconstructing device includes: a communicator for receiving sequential 2D images with an arbitrary slice gap; a sliced image generator for generating at least one sliced image positioned between the 2D images based on a feature point of the adjacent 2D images; and a controller for reconstructing the 2D image into a 3D image by use of the generated sliced image and providing the 3D image.

12 Claims, 9 Drawing Sheets

(51) Int. Cl.
*G06T 3/4007* (2024.01)
*G06T 15/00* (2011.01)

(52) U.S. Cl.
CPC .. *G06T 7/0012* (2013.01); *G06T 2207/20081* (2013.01); *G06T 2207/20084* (2013.01); *G06T 2211/416* (2013.01)

(58) Field of Classification Search
CPC ... G06T 2211/416; G06T 15/00; G06F 18/21; G06V 2201/03; G06V 10/82; G06V 20/64; A61B 5/055
USPC ......................................................... 382/154
See application file for complete search history.

(56) References Cited

U.S. PATENT DOCUMENTS

| | | | |
|---|---|---|---|
| 2012/0093280 A1* | 4/2012 | Konno | G01T 1/2985 378/7 |
| 2012/0275675 A1 | 11/2012 | Piron et al. | |
| 2013/0184569 A1* | 7/2013 | Strommer | G06T 7/30 600/424 |
| 2018/0085002 A1 | 3/2018 | Glinec et al. | |
| 2019/0318476 A1* | 10/2019 | Isgum | G16H 50/20 |
| 2020/0320685 A1* | 10/2020 | Anssari Moin | G06V 10/454 |
| 2021/0110584 A1* | 4/2021 | Claessen | G06T 7/0012 |

FOREIGN PATENT DOCUMENTS

| | | |
|---|---|---|
| KR | 10-1894278 | 9/2018 |
| KR | 10-1961177 | 3/2019 |
| WO | 2017-223560 | 12/2017 |

OTHER PUBLICATIONS

Seung Kwan Kang et al., "Deep learning Based 3D inpainting of brain MR images", Sci Rep 11, 1673, Jan. 18, 2021. https://doi.org/10.1038/s41598-020-80930-w.

* cited by examiner

FIG. 9
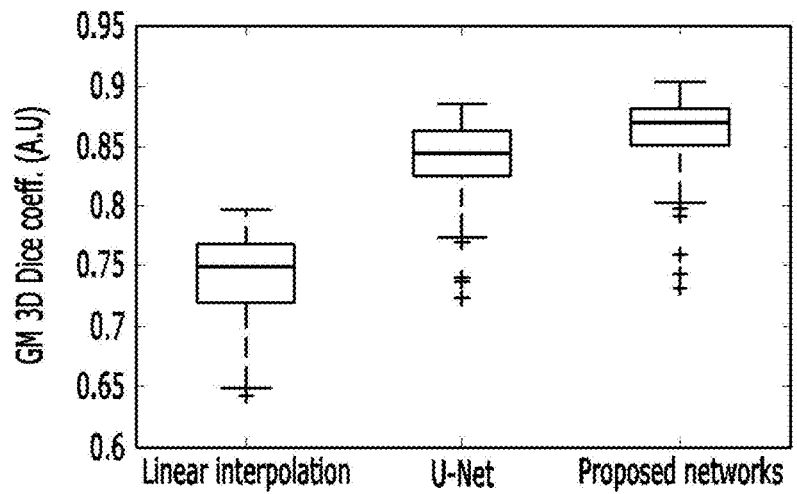
(a)
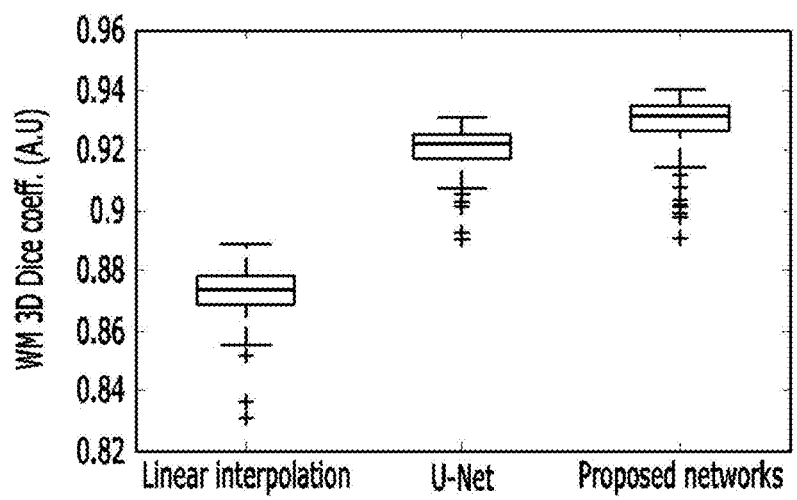
(b)
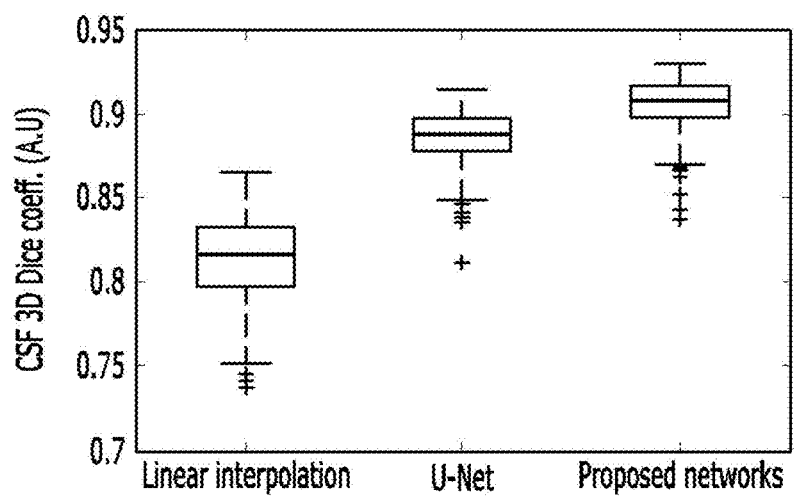
(c)

APPARATUS AND METHOD FOR RECONSTRUCTING THREE-DIMENSIONAL IMAGE

TECHNICAL FIELD

The present disclosure relates to a 3D image reconstructing device and a method thereof.

BACKGROUND ART

A three-dimensional (3D) image is widely used to diagnose patients and predict diseases in medical images, and its necessity is gradually increasing. However, it has many difficulties in acquiring high-quality 3D images. Particularly, sufficient capacity for storing data is needed and precise photographing must be performed, so it takes a long time to photograph, which is a drawback.

On the contrary, a 2-dimensional (2D) image is used the most frequently as it is obtained in the shortest time. Therefore, to obtain 3D images as well as an MRI, a method for increasing a size of a slice through 2D photographing, and thereby acquiring an image that is sparse in a 3D one-axis direction, is used.

Accordingly, a detailed structure may be found from the photographed sliced image, but it is difficult to estimate the image between the photographed slices in a quantitative or qualitative way.

In addition, to efficiently solve complicated and difficult problems in many fields, researches on artificial deep learning algorithms based on big data are in progress. Particularly, they may be effectively applied to the field of interpolation, generation, and reconstruction of data when the data are predicted based on existing materials and corresponding data are classified.

Hence, it is required to reconstruct the 2D image into a 3D image by using the artificial neural network.

Disclosure

The present invention has been made in an effort to accurately and quickly recover detailed information between slices of a 2D medical image and provide a quality-improved three-dimensional medical image.

An embodiment of the present invention may be used to achieve objects which are not specifically mentioned other than the above-mentioned object.

An embodiment of the present invention provides a three-dimensional reconstructing device including: a communicator for receiving sequential 2D images with an arbitrary slice gap; a sliced image generator for generating at least one sliced image positioned between the 2D images based on a feature point of the adjacent 2D images; and a controller for reconstructing the 2D image into a 3D image by use of the generated sliced image and providing the 3D image.

The sliced image generator may generate the sliced image positioned between the 2D images into a 3D image by repeating a process for selecting a voxel data group from the 2D image and applying the selected voxel data group to a learned deep learning algorithm.

The three-dimensional reconstructing device may further include a learner for teaching a deep learning algorithm based on raw data when at least one sliced image positioned between the secondary learning data is generated by applying 2D learning data generated based on the raw data of the 3D image to the deep learning algorithm.

When linear interpolation is performed on the 2D learning data, a sliced image positioned between linearly interpolated and adjacent 2D learning data is generated, and an error with the raw data corresponding to the generated sliced image is calculated to verify whether they correspond to each other, the learner may adjust weight values of a plurality of filters included in the deep learning algorithm, and may repeatedly teach so that the sliced image with the error value that is equal to or less than a threshold value is generated.

The learner may deduce a parameter for minimizing a loss function deduced according to an equation given below so as to maintain fidelity between an input and an output when generating a super-high-resolution sliced image in the deep learning algorithm.

$$L = \gamma_1 L_{WGAN-GP} + L_{fid} + \gamma_2 L_{per}$$

$$L_{fid} = \frac{1}{mn_v} \sum_{i=1}^{m} \sum_{j=1}^{n_v} \left\| y_j^i - f_j(x_s^i) \right\|_1$$

$$L_{per} = \frac{1}{2} \sum_{i=1}^{m} \left\| \phi(y^i) - \phi(f(x_s^i)) \right\|_2^2$$

Here, m is a disposal size, $n_v$ is a number of voxels, y is reference data, $x_s$ is a sparsely sampled input, f is a generative network, $L_{fid}$ is a fidelity loss, $L_{per}$ is a perceptual loss in a feature space, $\phi$ is a feature map for performing a middle function of a specific neural network, and $\gamma_2$ is a tuning parameter on the loss function.

The sliced image generator may generate a sliced image based on a predetermined filter applied gap when made into a block corresponding to a voxel data group of the 2D image, and a feature of each block in a convolution and a feature of each block in a deconvolution are connected to generate a high resolution voxel data group of the sliced image in the deep learning algorithm.

The sliced image generator may generate a sliced image for calculating a minimized loss value to which a deduced parameter is applied by using a WGAN-GP loss function including a gradient penalty term, a fidelity loss function, and a perceptual loss function.

Another embodiment of the present invention provides a method for reconstructing a 3D image of a three-dimensional reconstructing device including: receiving sequential 2D images with an arbitrary slice gap; generating at least one sliced image positioned between the adjacent 2D images based on a feature point between the 2D images; and reconstructing the 2D image into a 3D image by using the generated sliced image and providing the 3D image.

According to the embodiment of the present invention, when the diagnosis or study on the patients is progressed, a quantitative and statistical analysis may be performed with a low cost by reconstructing information between the 2D images and accurately recovering and providing detailed information.

According to the embodiment of the present invention, physiological and anatomical indexes, such as the thickness of the cerebral cortex, that were difficult to check from the image with a slice gap with more than a predetermined thickness, may be deduced in detail and in the quantitative way.

According to the embodiment of the present invention, detailed information on the portion that is lost when a three-dimensional medical image is photographed may be accurately and quickly recovered to thus provide the three-dimensional medical image.

DESCRIPTION OF THE DRAWINGS

FIG. 9 shows a graph for comparing 3D dice coefficients on an image reconstruction result described with reference to FIG. 8.

MODE FOR INVENTION

Figure 1:
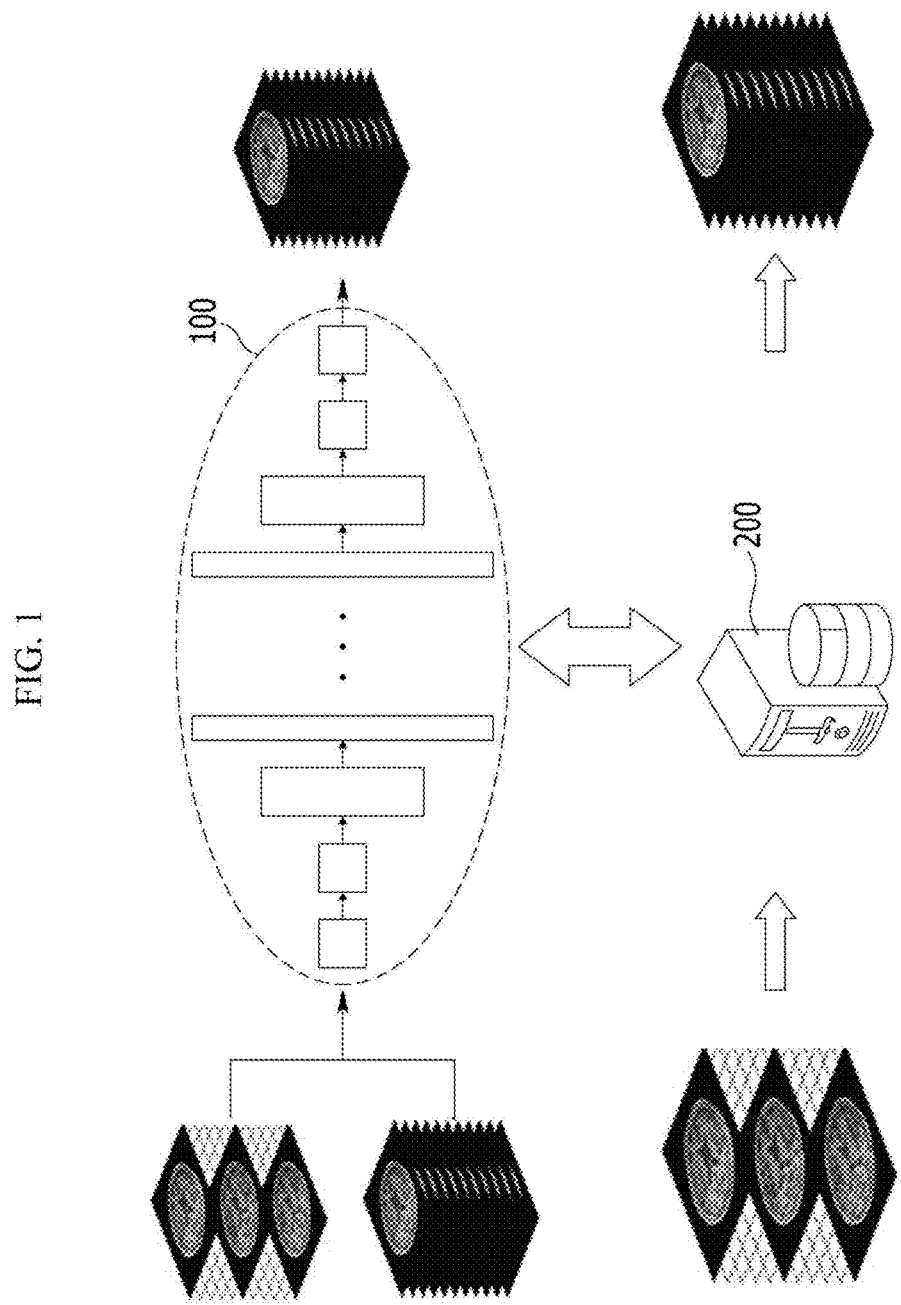
FIG. 1 shows a schematic view of a three-dimensional reconstructing device for reconstructing an image according to an embodiment of the present invention.

The present invention will be described more fully hereinafter with reference to the accompanying drawings, in which embodiments of the invention are shown. As those skilled in the art would realize, the described embodiments may be modified in various different ways, all without departing from the spirit or scope of the present invention. Parts that are irrelevant to the description will be omitted to clearly describe the present invention, and the same elements will be designated by the same reference numerals throughout the specification. A detailed description of a well-known related art will be omitted.

Unless explicitly described to the contrary, the word "comprise" and variations such as "comprises" or "comprising" will be understood to imply the inclusion of stated elements but not the exclusion of any other elements.

FIG. 1 shows a schematic view of a three-dimensional reconstructing device for reconstructing an image according to an embodiment of the present invention.

As shown in FIG. 1, the three-dimensional reconstructing device 200 receives a 2D image, and reconstructs the 2D image into a 3D image according to a previously learned deep learning algorithm 100.

Here, the 2D image signifies a set of a sequence of 2D images on a subject, and the 2D images respectively have an arbitrary slice gap.

For example, the three-dimensional reconstructing device 200 may receive a magnetic resonance imaging (MRI) image for showing a 2D cross-sectional image, and may reconstruct the same into a 3D MRI image according to a previously learned deep learning algorithm 100.

In addition, the three-dimensional reconstructing device 200 may perform learning for building a deep learning algorithm 100 before reconstructing the image.

In this instance, a 3D image and a 2D image for a same image are prepared as learning data, and the deep learning algorithm 100 may be taught so that the 2D image may be reconstructed in a like manner of the 3D image when a sliced image between 2D images is generated.

For example, the deep learning algorithm 100 may learn to find, through optimization, a parameter for minimizing an objective function that is set while a domain and a codomain of a function are respectively given as data according to supervised learning from among machine learnings.

The deep learning algorithm 100 may estimate how well the function is learned by inputting test data that are independently configured from the learning data.

The deep learning algorithm 100 may include a convolutional neural network (CNN) known to be specific to image processing, a generative adversarial network (GAN), and a Wasserstein GAN (WGAN).

Examples of the convolution neural network (CNN) include the VGGNet, the ResNet, the DnCNN, and the DenseNet, and the generative adversarial network (GAN) learns according to contests of two neural network models of a generator (G) and a discriminator (D) and generates a resulting material.

The generator (G) aiming at generating data that are close to reality, learns actual data, and generates data based on it, and the discriminator (D) learns to distinguish whether the data generated by the generator (G) are real or false.

The WGAN-GP is an improve algorithm of the WGAN, and it adds a penalty term for applying k-Lipschitz constraints.

It will be described hereinafter that the three-dimensional reconstructing device 200 reconstructs the 2D image into a 3D one by using the deep learning algorithm of the WGAN_GP, but is not limited thereto.

In detail, a loss function ($L_{WGAN\text{-}GP}$) of the WGAN_GP applied to the three-dimensional reconstructing device 200 is expressed in Equation 1.

$$L_{WGAN\text{-}GP} = \mathbb{E}_{\tilde{x} \sim P_g}[D(\tilde{x})] - \mathbb{E}_{x \sim P_r}[D(x)] + \lambda \mathbb{E}_{\hat{x} \sim P_{\hat{x}}}[(\|\nabla_{\hat{x}} D(\hat{x})\|_2 - 1)^2]$$

[Equation 1]

Here, E is an expected value from a given distribution, "~" mark signifies a sample obtained from the distribution, and $\tilde{x}$ indicates generated data. $P_g$ is a distribution of generated data, x and $P_r$ represent actual data, and a parameter of λ is set to be 10. $\hat{x}$ is an arbitrarily interpolated value and is realized with a sum of uniform samplings of 0 to 1 and weight values. D is a determination network, and represents a logic function for determining a real or false value.

In Equation 1, the first and second terms are used to minimize a Wasserstein distance between the generated data and the actual data distribution so that the network may generate a further realistic sample between the actual data distribution.

The last term realizes the 1-Lipschitz constraints by calculating a slope of the logic function on $\hat{x}$ realized by use of automatic discrimination in a tensor flow.

A three-dimensional reconstructing device for reconstructing a 2D image into a 3D image by using a deep learning algorithm and providing the same will now be described in detail with reference to FIG. 2.

Figure 2:
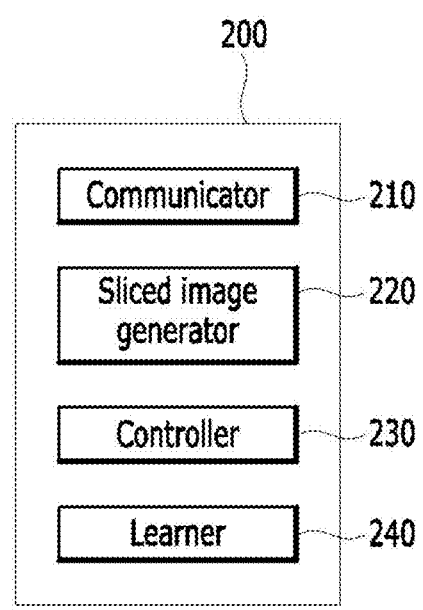
FIG. 2 shows a schematic diagram of a three-dimensional reconstructing device according to an embodiment of the present invention.

FIG. 2 shows a schematic diagram of a three-dimensional reconstructing device according to an embodiment of the present invention.

As shown in FIG. 2, the three-dimensional reconstructing device 200 includes a communicator 210, a sliced image generator 220, a controller 230, and a learner 240.

The communicator 210 may be connected to a terminal such as a linking image photographing device, a medical device, or a medical image storage system, or a server through a network, and may transmit or receive data.

In this instance, the transmitted or received data represent sequential 2D images, slices, or sliced images, and without being limited thereto, they may include tomographic images of the 3D image having a slice gap that is equal to or greater than a predetermined value.

The sliced image generator 220 generates at least one sliced image positioned between adjacent 2D images based on a feature point among the 2D images.

In this instance, the sliced image generator 220 generates the sliced image by applying a weight value adjusted according to the learned deep learning algorithm. The sliced image generator 220 may generate at least one sliced image between the generated sliced image and the 2D image.

The sliced image generator 220 may repeatedly generate sliced images so as to have an input or predetermined slice gap, and the sliced images may be generated as 3D images. In this instance, when a high-resolution voxel data group of a sliced image is generated corresponding to a voxel data group of a 2D image, ad the sliced image generator 220 may generate the sliced image by repeatedly applying it based on a predetermined filter applied gap.

The controller 230 reconstructs the 2D image into a 3D image by using the generated sliced image and provides the 3D image. The generated sliced image is formed to be the 3D image, and the received 2D image may be reconstructed into the 3D image by using the three-dimensional sliced image and the 3D image.

The learner 240 learns the deep learning algorithm in advance by using the learning data.

The learner 240 may generate learning data by receiving learning data and raw data that are a 3D image of the corresponding learning data or using the raw data that are the received 3D image.

For example, the learner 240 may generate 2D learning data extended to be a 2D image so that the slice gap of the raw data of the 3D image having the slice gap that is equal to or less than a first threshold value may become equal to or greater than a second threshold value.

Here, the first threshold value is greater than the second threshold value, and the respective threshold values may be easily modified and designed by a user according to conditions to be learned.

The learner 240 may learn the learned deep learning algorithm again for respective time gaps or predetermined periods to perform an update.

Further, the learner 240 may verify accuracy corresponding to the reconstructed 3D image. When accuracy is verified, as expressed in Equation 2, a peak signal-to-noise ratio (PSNR), structural similarity (SSIM), and a high frequency error norm (HFEN) may be used regarding image quality.

$$PSNR = 10\log_{10}\left(\frac{\max(I_y)}{MSE}\right)$$

[Equation 2]

$$SSIM = \frac{(2\mu_x\mu_y + c_1)(2\sigma_{xy} + c_2)}{(\mu_x^2 + \mu_y^2 + c_1)(\sigma_x^2 + \sigma_y^2 + c_2)}$$

$$HFEN = \frac{\|LoG(I_x) - LoG(I_y)\|_2}{\|LoG(I_y)\|_2}$$

Here, $I_x$ is a test image, $I_y$ is a reference image, MSE is a mean squared error between them, $\mu_{(\cdot)}$ and $\sigma_{(\cdot)}$ are a mean and a variance or a covariance of two images, $c_1=(0.01\times d)^2$, and $c_2=(0.03\times d)^2$.

Further, d is a maximum difference of image intensity, LoG (•) is a 3D Laplacian of Gaussian filter function, and a size of a filter kernel is given as 15 pixels×15 pixels×15 pixels.

In this instance, the learner 240 has been described to be included in the three-dimensional reconstructing device 200, and a terminal that learns according to an applied field and a condition, a server, or a device may be separately provided.

The three-dimensional reconstructing device 200 may be a server, a terminal, or a combined form thereof.

The terminal is collectively referred to as a device that includes a memory and a processor and has operational processing performance. For example, it includes a personal computer, a handheld computer, a personal digital assistant (PDA), a mobile phone, a smart device, and a tablet.

The server may include a memory in which a plurality of modules are stored, a processor connected to the memory, reacting to the modules, and processing service information provided to the terminal or action information for controlling the service information, a communication means, and a user interface (UI) displaying means.

The memory stores information, and it may include various types of memories including a high-speed random access memory, a magnetic disk storing device, a flash memory device, and a non-volatile memory such as a non-volatile solid-state memory device.

The communication means transmits and receives service information or action information to/from the terminal in real-time.

The UI displaying means outputs service information or action information of the device in real-time. The UI displaying means may be an individual device for directly or indirectly outputting or displaying the UI, or it may be part of a device.

A process for generating a sliced image between 2D images of a three-dimensional reconstructing device 200 and reconstructing the same into a 3D image will now be described in detail.

Figure 3:
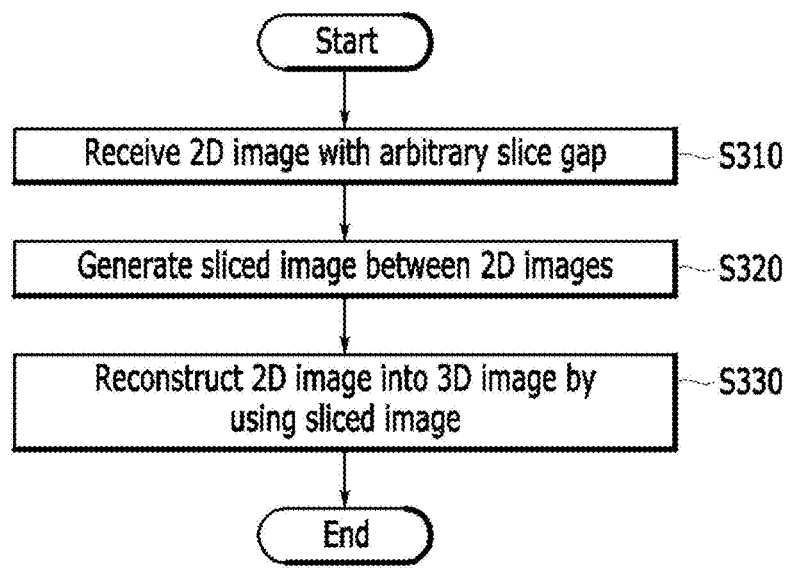
FIG. 3 shows a flowchart of a method for reconstructing an image by a three-dimensional reconstructing device according to an embodiment of the present invention.

FIG. 3 shows a flowchart of a method for reconstructing an image by a three-dimensional reconstructing device according to an embodiment of the present invention.

The three-dimensional reconstructing device 200 receives a 2D image with an arbitrary slice gap (S310).

The three-dimensional reconstructing device 200 may determine whether the received 2D image is a 2D image that has a slice gap that is equal to or greater than a predetermined gap.

For example, the three-dimensional reconstructing device 200 may collect photographed images in linkage to respective medical devices, and may access a database (not shown) to collect images.

The three-dimensional reconstructing device 200 may perform linear interpolation on the 2D image.

The three-dimensional reconstructing device 200 generates a sliced image between 2D images (S320).

In this instance, the three-dimensional reconstructing device 200 may generate at least one sliced image positioned between 2D images into a 3D image by using the learned deep learning algorithm. Here, the deep learning algorithm is learned before the step S310 by the three-dimensional reconstructing device 200 or an additional terminal or a server.

A process for a three-dimensional reconstructing device 200 to learn a deep learning algorithm, and a learned deep learning algorithm, will now be described with reference to FIG. 4 and FIG. 5.

Figure 4:
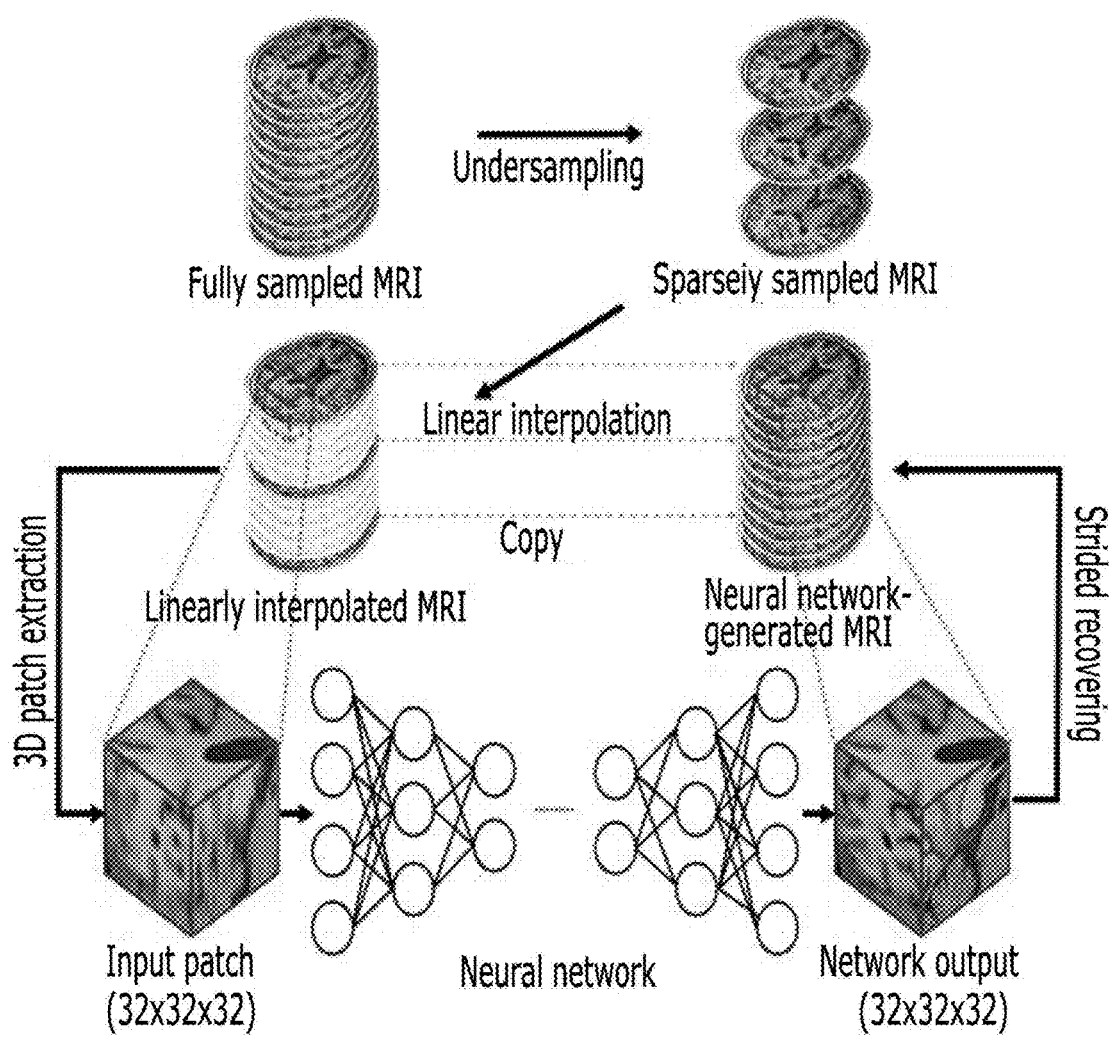
FIG. 4 shows a deep learning-based method for reconstructing a 2D medical image into a three-dimensional one according to an embodiment of the present invention.
Figure 5:
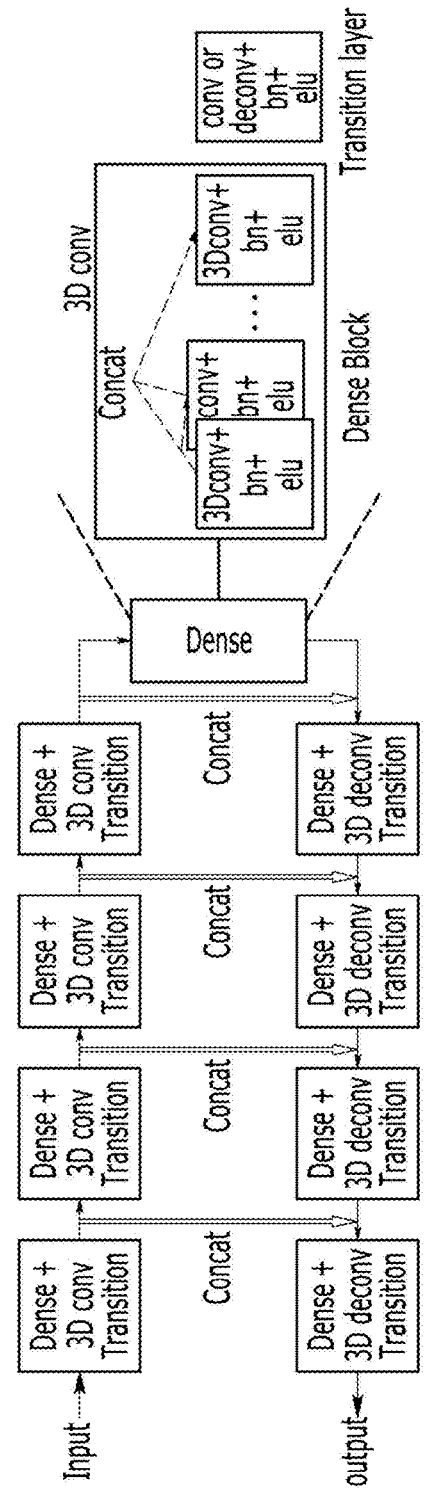
FIG. 5 shows a structure of a neural network according to an embodiment of the present invention.

FIG. 4 shows a deep learning-based method for reconstructing a 2D medical image into a three-dimensional one according to an embodiment of the present invention, and FIG. 5 shows a structure of a neural network according to an embodiment of the present invention.

As shown in FIG. 4, the three-dimensional reconstructing device 200 learns raw data (fully sampled MRI) of the 3D image with the slice gap that is equal to or less than the first threshold value by using 2D learning data (sparsely sampled MRI) that are extended to the 2D image so that the slice gap may be equal to or greater than the second threshold value.

The three-dimensional reconstructing device 200 samples the reference image for each fifth slice in an axis direction. The three-dimensional reconstructing device 200 performs linear interpolation so as to compare the same with a high resolution image generated according to the deep learning algorithm.

The three-dimensional reconstructing device 200 may extract a voxel data group (3D patch) from the linearly interpolated 2D learning data (linearly interpolated MRI) and may apply the same to the deep learning algorithm as an input value.

In other words, regarding the deep learning algorithm learned and applied by the three-dimensional reconstructing device 200, an input value is applied in a form (32×32×32) of the voxel data group (3D patch), and an output value is deduced in the same form (32×32×32) of the voxel data group (3D patch). Here, the form of the voxel data group is an example and is not limited thereto.

For example, when a center of the voxel data group (3D patch) is in the extracted brain image, the three-dimensional reconstructing device 200 extracts the input voxel data group of the size of 32×32×32 from the linearly interpolated data for training in which a stride (a filter applied gap) is set to be 16. In this instance, the three-dimensional reconstructing device 200 may normalize input image intensity in a range of −1 to 1. By repeating the above-noted process, the three-dimensional reconstructing device 200 may acquire the total number of 439,479 of training patches with a disposal size of 12.

As shown in FIG. 5, for example, the deep learning algorithm (i.e., a neural network) may be configured with nine high-density blocks and transition layers. Regarding the deep learning algorithm, the respective dense blocks with five convolution layers are connected to the next transition layer.

Here, the next transition layer may signify four blocks with a stride-applied convolution transition layer, a block without a transition layer, and four blocks with a deconvolution transition layer.

In other words, the convolution layer of the deep learning algorithm may connect the layer included in the process to maintain a function of the previous layer.

In this instance, feature values of the blocks may be connected to each other corresponding to the case in which the convolution layer has the same size as the deconvolution layer.

Hence, the convolution layer may be expressed as Equation 3.

$$x_l = H_l([x_0, x_1, \ldots, x_{l-1}])$$  [Equation 3]

Here, $x_l$ shows the feature value of the $i^{th}$ layer, and $H_l$ shows a structure of an activation function (an exponential linear unit) and a batch normalization of the $l^{th}$ layer.

As expressed in Equation 3, the three-dimensional reconstructing device 200 arranges respective structures into blocks (voxel data group/3D patch) so as to use a DenseNet structure for generating a deeper network. The three-dimensional reconstructing device 200 may connect the respective blocks like a short-cut path.

In detail, as shown in FIG. 4 and Equation 3, respective convolution operations of the blocks with a high density are connected to include previous output values, and channels with the same number are generated, so the connection of the previous layer may increase the number of input channels of the next layer.

Therefore, a process for compressing data by applying the convolution of 1×1×1 and the convolution of 3×3×3 is performed.

For example, when there are sixteen channels in the first high-density block layer, the transition layers following the first four dense blocks sample the sub-sampled image by using the convolution of (2×2×2) to acquire a larger receptive field. On the contrary, the deconvolution (transitioned convolution) transition layer links to the convolution block in the final four dense blocks.

In other words, the feature calculated in the convolution of applying a stride with dense blocks is connected to the feature of the dense block of the deconvolution for reversely propagating the gradient so as to maintain the same number in the respective convolutions.

Particularly, the deep learning algorithm applied in the present invention includes a verification network for verifying an actual data set and a data set generated for generating a realistic data set that may not be distinguished.

For example, the verification network may be configured with eight 3D convolution layers, instant normalization, and a leaked rectified linear unit.

The verification network may be configured with a single layer completely connected at an end of the network.

As described, the three-dimensional reconstructing device 200 realizes a different deep learning algorithm by using the convolution to which the stride is applied and not the maximum pooling.

The three-dimensional reconstructing device 200 optimizes the deep learning algorithm by using Equation 4, so as to maintain fidelity between an input and an output when the deep learning algorithm generates a super-high-resolution sliced image.

$$L = \gamma_1 L_{WGAN-GP} + L_{fid} + \gamma_2 L_{per}$$  [Equation 4]

$$L_{fid} = \frac{1}{mn_v} \sum_{i=1}^{m} \sum_{j=1}^{n_v} \left\| y_j^i - f_j(x_s^i) \right\|_1$$

$$L_{per} = \frac{1}{2} \sum_{i=1}^{m} \left\| \phi(y^i) - \phi(f(x_s^i)) \right\|_2^2$$

Here, m is a disposal size, $n_v$ is a number of voxels, y is reference data, $x_s$ is a sparsely sampled input, and f is a generative network. $L_{fid}$ is a fidelity loss, and may reduce a content difference between a reference of the generative network and the output. $L_{per}$ is a perceptual loss of a feature space, $\phi$ is a feature map for performing a middle function of a specific neural network, and $\gamma_2$ is a tuning parameter on the loss function.

In this instance, for a fast training, the perceptual loss may be estimated by using the center slice of the input patch. A total loss of the network education may be obtained as a sum of the fidelity and the perceptual loss after the above-noted process.

Here, the three-dimensional reconstructing device 200 uses the $L_{per}$ (perceptual loss) and the $L_{WGAN-GP}$ compared to the existing neural network algorithm (e.g., U-Net) for optimizing the algorithm by using the $L_{fid}$. Here, the $L_{per}$ and the $L_{WGAN-GP}$ improve accuracy of the generated image, and may particularly improve accuracy on the detailed structure such as gray matter and white matter of the brain.

Therefore, the three-dimensional reconstructing device 200 may deduce the parameter (filter weight value) optimized according to repeated learning so that the loss function (L) may be minimized in Equation 4.

When the optimized parameter is deduced, the three-dimensional reconstructing device 200 completes the learning, and may store a parameter on the learned deep learning algorithm in a linking database.

The three-dimensional reconstructing device 200 may generate a plurality of sliced images on the received 2D image by using the deep learning algorithm learned in advance.

In this instance, the sliced image signifies an image connected between the 2D images.

The three-dimensional reconstructing device 200 may generate a first sliced image between the 2D images, may generate a second sliced image between the 2D image and the first sliced image, and by repeating in the same way, it may generate a plurality of sliced images with the gap of the sliced image between the 2D images that is equal to or less than a first threshold value.

The three-dimensional reconstructing device 200 reconstructs the 2D image into a 3D image by using the sliced image (S330).

The three-dimensional reconstructing device 200 may transmit the corresponding 3D image to the linked user terminal or the server when sequentially reconstructing a plurality of sliced images into the 3D image.

The three-dimensional reconstructing device 200 may learn the deep learning algorithm that is learned according to a predetermined gap, and may update weight values applied to the respective layers.

Accuracy of the three-dimensional reconstructing device will now be described in detail with reference to FIG. 6 to FIG. 9.

Figure 6:
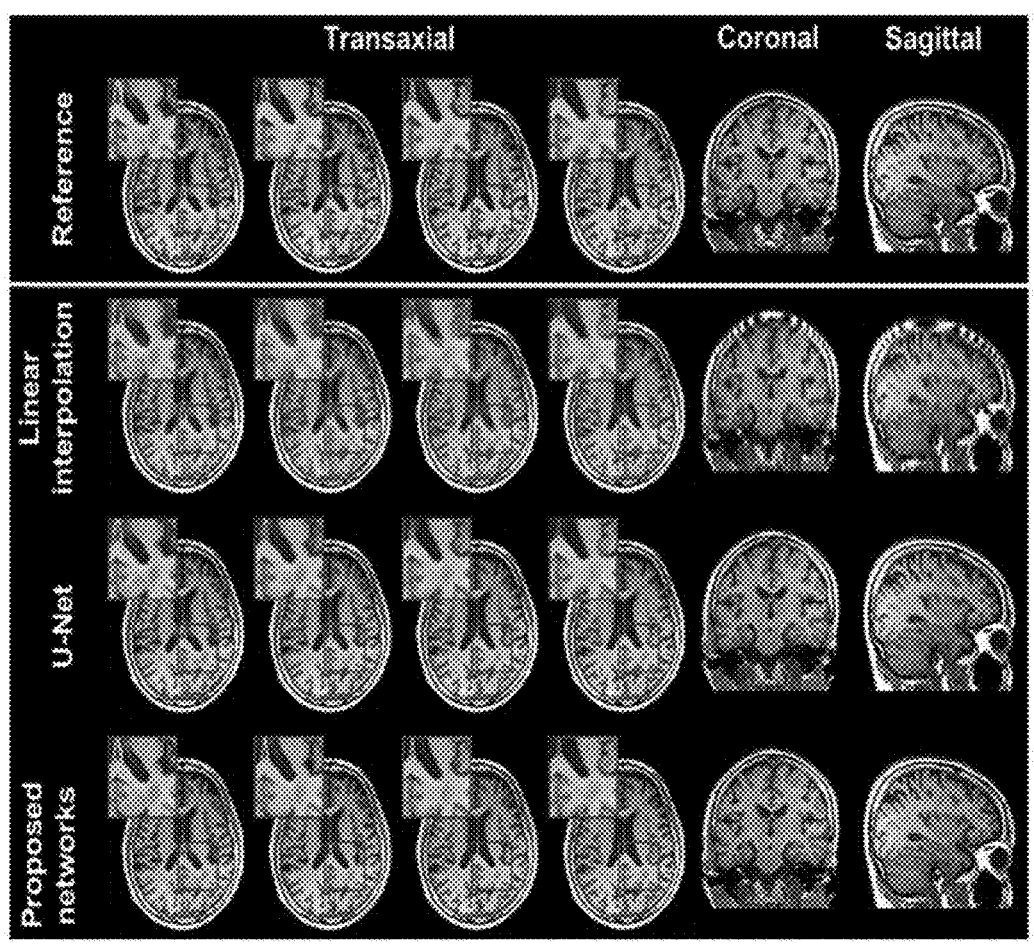
FIG. 6 shows a three-dimensional reconstructing method, linear interpolation, and a reconstruction result through a U-net according to an embodiment of the present invention.
Figure 7:
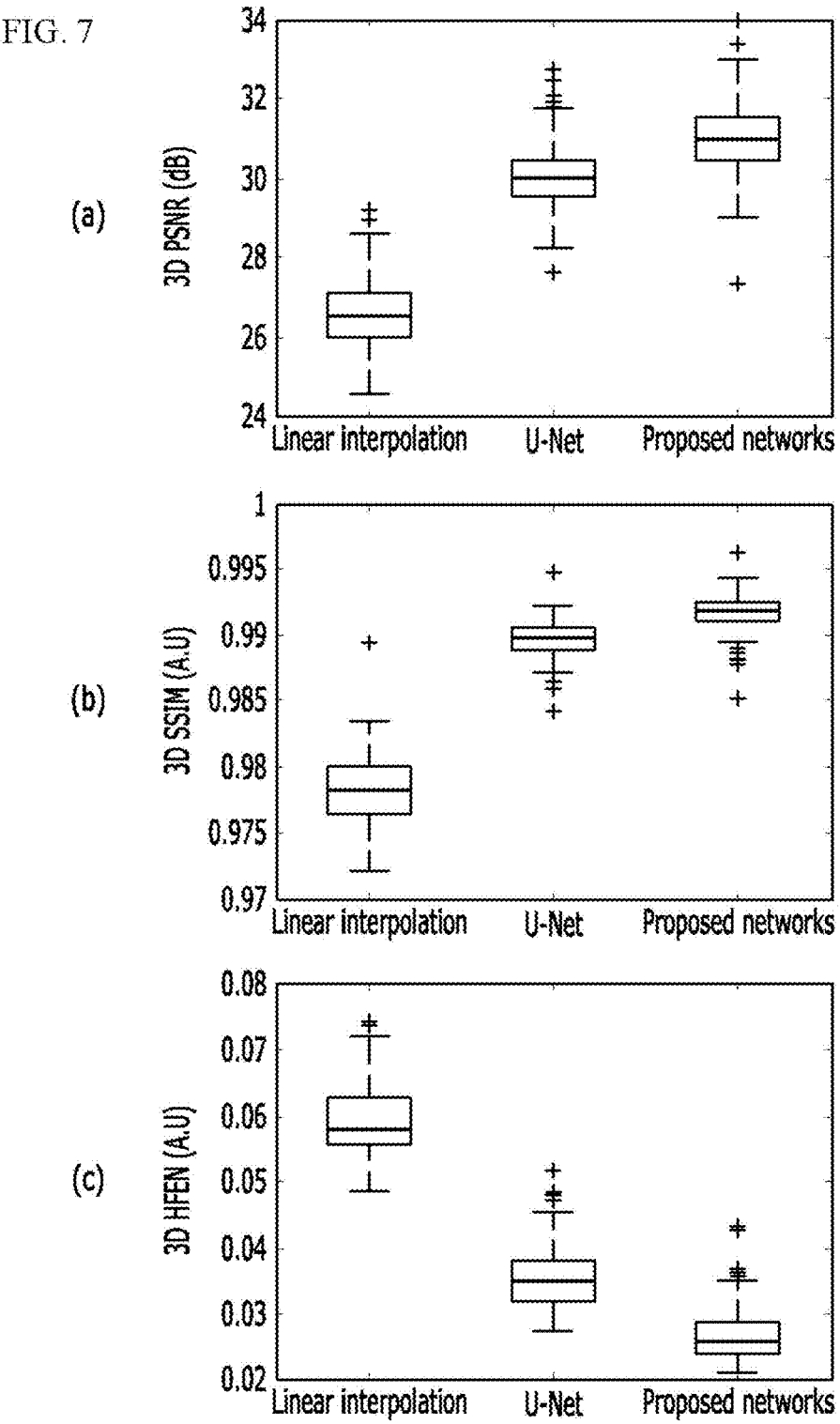
FIG. 7 shows a graph of an accuracy estimation result on an image reconstructing result described with reference to FIG. 6.

FIG. 6 shows a reconstruction result through a three-dimensional reconstructing method, linear interpolation, and a U-net according to an embodiment of the present invention, and FIG. 7 shows a graph of an accuracy estimation result on an image reconstruction result described with reference to FIG. 6.

As shown in FIG. 6, a reconstructed result into a 3D image according to a linear interpolation on the reference data, a U-NET algorithm, and a three-dimensional reconstructing method (i.e., proposed networks) according to the present invention on a coronal plane (Coronal), a sagittal plane (Sagittal), and a transaxial plane (Transaxial) of the brain is given.

Referring to FIG. 6, respective columns represent the 137-th to 140-th slices on the transaxial plane (the horizontal plane), and indicate the 95-th slice on the coronal plane and the 125-th slice image on the sagittal plane.

Regarding the reconstructed result according to the linear interpolation, the U-net, and the present invention, the result reconstructed by the linear interpolation has low accuracy while the accuracy is very high when the 3D image is reconstructed according to the U-net and the method proposed by the present invention.

Among them, it is found that the reconstructed 3D image according to the method proposed by the present invention shows higher accuracy in detailed portions than the case of using the U-net. For example, when the 138-th (second one from the left) image on the transaxial plane (the horizontal plane) is checked, a shadow form that is not in the image according to the reference data and the method proposed by the present invention is shown in the U-net.

Also, as shown in FIG. 7, accuracy on various super-resolution (SR) methods on the reference data may be estimated.

(a) of FIG. 7 shows a graph of a peak signal to noise ratio (PSNR) of a 3D image according to a linear interpolation, a U-net, and a method proposed by the present invention.

Referring to (a) of FIG. 7, it is found that the method proposed by the present invention has the highest PSNR value. Here, the PSNR is a parameter value for measuring quality of the image, and when noise of the image is 0, the PSNR may have an infinite value. In other words, the greater the PSNR value is, the higher the quality of the image may be estimated to be.

(b) of FIG. 7 shows a graph of a structural similarity metric (SSIM) of a 3D image, and similarity between 3D images reconstructed by the reference data and the various methods is estimated. It is found in (b) of FIG. 7 that the method proposed by the present invention has the highest similarity.

(c) of FIG. 7 shows a graph of a high frequency error norm (HFEN) of a 3D image, and it is found that the method proposed by the present invention has the lowest similarity.

Figure 8:
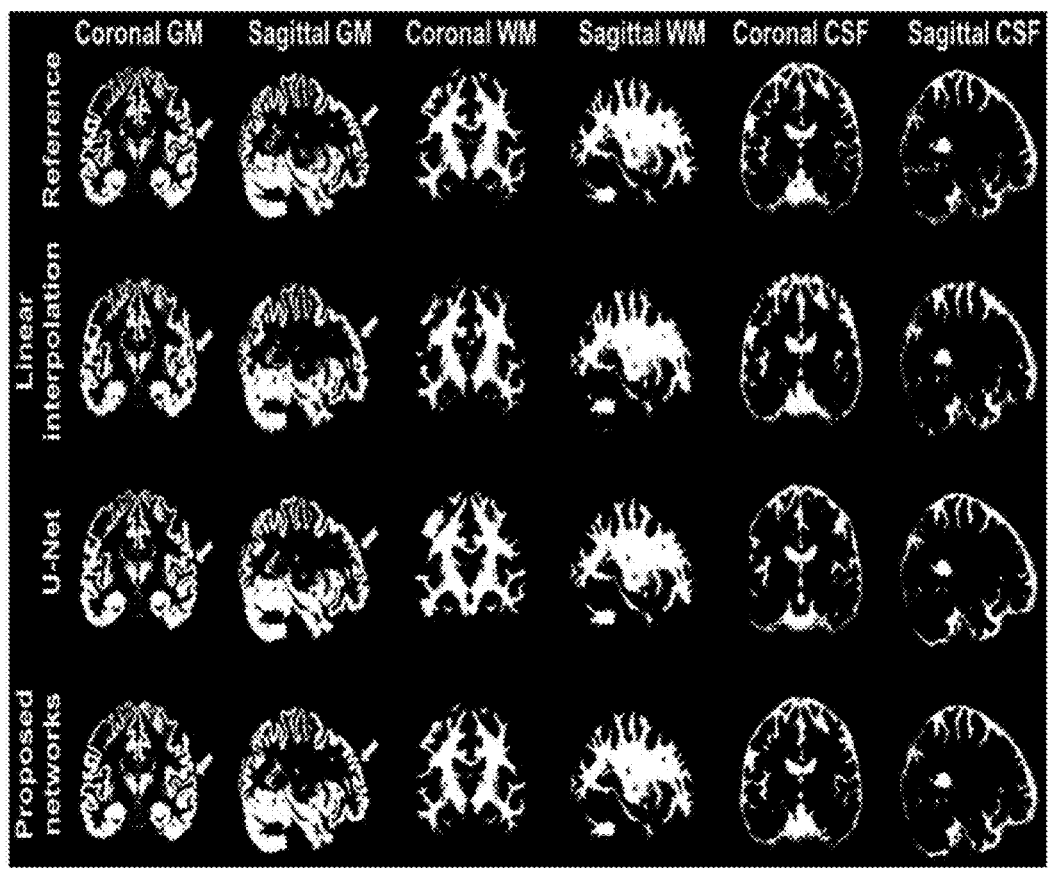
FIG. 8 shows a method for three-dimensional reconstructing a brain image according to an embodiment of the present invention, linear interpolation, and a reconstruction result through a U-net.

FIG. 8 shows a method for three-dimensional reconstructing a brain image according to an embodiment of the present invention, linear interpolation, and a reconstruction result through a U-net, and FIG. 9 shows a graph for comparing 3D dice coefficients on an image reconstruction result described with reference to FIG. 8.

As shown in FIG. 8, a reconstructed result into a 3D image according to the linear interpolation on the reference data, the U-NET algorithm, and the three-dimensional reconstructing method (proposed networks) of the present invention on the coronal gray matter (GM), the sagittal gray matter (GM), the coronal white matter (WM), the sagittal white matter (WM), the coronal cerebrospinal fluid (CSF), and the sagittal cerebrospinal fluid (CSF) is given.

Regarding a yellow arrow given in FIG. 8, in the case of the linear interpolation and the U-net method, it is found that recovery of the gray matter (GM) segment is not precise compared to the reference data. On the other hand, it is found that the method proposed in the present invention precisely reconstructs the image on the reference data.

Referring to FIG. 9, a 3D dice coefficient between the reference data and the reconstructed super-resolution image is shown, and the 3D dice coefficient according to the method proposed in the invention corresponding to the gray matter (GM), the white matter (WM), and the cerebrospinal fluid (CSF) is found to be the highest.

For reference, the 3D dice coefficient is one of criteria for estimating performance of models, and the performance is measured to be better as its value approaches 1, while it is measured to be worse as its value approaches 0.

As described above, according to the present invention, the 3D image reconstructing device 200 may generate the sliced image with high accuracy through the learned neural network to thus more quickly and efficiently generate the three-dimensional medical image with improved quality.

A program for performing the method according to an embodiment of the present invention may be recorded on a computer readable medium.

The computer readable medium may include a program instruction, a data file, a data structure, and a combination thereof. The medium may be that which is designed and configured for a special purpose, or that which is known to a person of ordinary skill in the art of computer software and is usable. Examples of the computer readable medium include magnetic media such as a hard disk drive, a floppy disk, or a magnetic tape, optical media such as a CD-ROM or a DVD, magneto-optical media such as a floptical disk, and a hardware device specially configured to store and execute program instructions such as a ROM, a RAM, or a flash memory. Here, the medium may be a transmission medium such as an optical line, a metal line, or a waveguide including a carrier for transmitting a signal for designating a program instruction or a data structure. Examples of the program instruction include high-level language codes executable by a computer by using an interpreter in addition to machine language codes generated by a compiler.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

| | |
|---|---|
| 100: deep learning algorithm | 200: 3D image reconstructing device |
| 210: communicator | 220: sliced image generator |
| 230: controller | 240: learner |

The invention claimed is:

1. A three-dimensional (3D) reconstructing device comprising:
 a communicator for receiving sequential 2D images with an arbitrary slice gap;
 a sliced image generator for generating at least one sliced image positioned between adjacent 2D images among the sequential 2D images based on a feature point of the adjacent 2D images; and
 a controller for reconstructing the sequential 2D images into a 3D image by use of the generated sliced image and providing the 3D image.

2. The three-dimensional reconstructing device of claim 1, wherein
 the sliced image generator generates the sliced image positioned between the adjacent 2D images into a 3D image form by repeating a process for selecting a voxel data group from the 2D image and applying the selected voxel data group to a learned deep learning algorithm.

3. The three-dimensional reconstructing device of claim 2, further comprising
 a learner for teaching a deep learning algorithm based on raw data when at least one sliced image positioned between the secondary learning data is generated by applying 2D learning data generated based on the raw data of the 3D image to the deep learning algorithm.

4. The three-dimensional reconstructing device of claim 3, wherein
 when linear interpolation is performed on the 2D learning data, a sliced image positioned between linearly interpolated and adjacent 2D learning data is generated, and an error with the raw data corresponding to the generated sliced image is calculated to verify whether they correspond to each other, the learner adjusts weight values of a plurality of filters included in the deep learning algorithm, and repeatedly teaches so that the sliced image with the error value that is equal to or less than a threshold value is generated.

5. The three-dimensional reconstructing device of claim 3, wherein
 the learner deduces a parameter for minimizing a loss function deduced according to an equation given below so as to maintain fidelity between an input and an output when generating a super-high-resolution sliced image in the deep learning algorithm:

$$L = \gamma_1 L_{WGAN-GP} + L_{fid} + \gamma_2 L_{per}$$

$$L_{fid} = \frac{1}{mn_v} \sum_{i=1}^{m} \sum_{j=1}^{n_v} \|y_j^i - f_j(x_s^i)\|_1$$

$$L_{per} = \frac{1}{2} \sum_{i=1}^{m} \|\phi(y^i) - \phi(f(x_s^i))\|_2^2$$

here, m is a disposal size, $n_v$ is a number of voxels, y is reference data, $x_s$ is a sparsely sampled input, f is a generative network, $L_{fid}$ is a fidelity loss, $L_{per}$ is a perceptual loss in a feature space, $\phi$ is a feature map for performing a middle function of a specific neural network, and $\gamma_2$ is a tuning parameter on the loss function.

6. The three-dimensional reconstructing device of claim 2, wherein
 the sliced image generator generates a sliced image based on a predetermined filter applied gap when made into a block corresponding to a voxel data group of the 2D image, and a feature of each block in a convolution and a feature of each block in a deconvolution are connected to generate a high resolution voxel data group of the sliced image in the deep learning algorithm.

7. The three-dimensional reconstructing device of claim 2, wherein
 the sliced image generator generates a sliced image for calculating a minimized loss value to which a deduced parameter is applied by using a WGAN-GP loss function including a gradient penalty term, a fidelity loss function, and a perceptual loss function.

8. A method for reconstructing a 3D image of a three-dimensional reconstructing device, comprising:
 receiving sequential 2D images with an arbitrary slice gap;
 generating at least one sliced image positioned between adjacent 2D images among the sequential 2D images based on a feature point between the adjacent 2D images; and
 reconstructing the sequential 2D image images into a 3D image by using the generated sliced image and providing the 3D image.

9. The method of claim 8, wherein
 the generating of at least one sliced image includes
 generating the sliced image positioned between the adjacent 2D images into a 3D image form by repeatedly performing a process for selecting a voxel data group in the 2D image and applying the selected voxel data group to a learned deep learning algorithm.

10. The method of claim 9, wherein
 the generating of at least one sliced image includes
 generating a sliced image based on a predetermined filter applied gap when made into a block corresponding to a voxel data group of the 2D image, and a feature of each block in a convolution and a feature of each block in a deconvolution are connected to generate a high resolution voxel data group of the sliced image in the deep learning algorithm.

11. The method of claim 9, wherein
the generating of at least one sliced image includes generating a sliced image for calculating a minimized loss value to which a deduced parameter is applied by using a WGAN-GP loss function including a gradient penalty term, a fidelity loss function, and a perceptual loss function.

12. The method of claim 8, further comprising
adjusting weight values of a plurality of filters included in a deep learning algorithm and repeatedly teaching so that the sliced image with the error value that is equal to or less than a threshold value is generated when a sliced image positioned between the 2D learning data generated based on raw data of a 3D image is generated, and an error with the raw data corresponding to the generated sliced image is calculated to verify whether they correspond to each other, before the receiving.

* * * * *